US008070798B2

(12) United States Patent
Wilcox et al.

(10) Patent No.: US 8,070,798 B2

(45) Date of Patent: Dec. 6, 2011

(54) DRUG ELUTING MEDICAL DEVICE AND METHOD

(76) Inventors: Josiah Wilcox, Santa Rosa, CA (US); Jeffrey Allen, Santa Rosa, CA (US); Scott Doig, Santa Rosa, CA (US); Rafaelita Brown, Santa Rosa, CA (US)

(*) Notice: Subject to any disclaimer, the term of this patent is extended or adjusted under 35 U.S.C. 154(b) by 346 days.

(21) Appl. No.: 11/780,572

(22) Filed: Jul. 20, 2007

(65) Prior Publication Data

US 2009/0024200 A1 Jan. 22, 2009

(51) Int. Cl.
*A61F 2/82* (2006.01)

(52) U.S. Cl. ........................................................ 623/1.44

(58) Field of Classification Search ......... 623/1.42–1.49
See application file for complete search history.

(56) References Cited

U.S. PATENT DOCUMENTS 4,827,940 A 5/1989 Mayer et al.
5,605,696 A 2/1997 Eury et al.
5,697,967 A 12/1997 Dinh et al.
6,131,580 A 10/2000 Ratner et al.
6,240,616 B1 * 6/2001 Yan .............................. 29/527.2
6,391,033 B2 5/2002 Ryan
6,626,933 B1 9/2003 Lau et al.
6,629,992 B2 10/2003 Bigus et al.
6,663,662 B2 12/2003 Pacetti et al.
6,749,628 B1 * 6/2004 Callol et al. ................. 623/1.15
7,465,315 B2 * 12/2008 Morris et al. ................ 623/1.15
7,488,444 B2 * 2/2009 Furst et al. ..................... 420/429
7,491,234 B2 * 2/2009 Palasis et al. ................ 623/1.42
7,517,362 B2 * 4/2009 Shanley et al. .............. 623/1.42
2002/0143392 A1 10/2002 Ryan
2003/0068355 A1 4/2003 Shanley et al.
2004/0234575 A1 11/2004 Horres et al.
2005/0176678 A1 8/2005 Horres et al.
2005/0192657 A1 * 9/2005 Colen et al. .................. 623/1.11
2007/0244548 A1 * 10/2007 Myers et al. ................. 623/1.42
2008/0255510 A1 * 10/2008 Wang ....................... 604/103.02

FOREIGN PATENT DOCUMENTS

EP 1364664 11/2003
WO WO2008/118605 10/2008

* cited by examiner

*Primary Examiner* — Suzette J Gherbi

(57) ABSTRACT

A drug elution stent includes a stent framework and a drug elution portion disposed on the stent framework. The drug elution portion includes a first sugar layer disposed on the stent framework, at least one therapeutic agent layer disposed on the first sugar layer and a second sugar layer disposed on the at least one therapeutic agent layer. A method of manufacturing a drug elution stent includes the steps of providing a stent having a stent framework and coating at least a portion of the stent framework with a drug elution portion. The drug elution portion includes a first sugar layer disposed on the stent framework, at least one therapeutic agent layer disposed on the first sugar layer and a second sugar layer disposed on the at least one therapeutic agent layer.

24 Claims, 5 Drawing Sheets

400

DRUG ELUTING MEDICAL DEVICE AND METHOD

TECHNICAL FIELD

This invention relates generally to implantable drug delivery medical devices, and more particularly to drug delivery stents.

BACKGROUND OF THE INVENTION

Drug coated stents can improve the overall effectiveness of angioplasty and stenotic procedures performed on the cardiovascular system and other vessels within the body by delivering potent therapeutic compounds to a target site. Anti-inflammatory and anti-thrombogenic drugs may be carried on the stent and released gradually after insertion and deployment of the stent. These drugs and coatings can reduce the trauma to the local tissue bed, aid in the healing process, and significantly reduce the recurrence of narrowing or constriction of the blood vessel that after stent delivery and placement.

It is desirable to have a medicated stent that can be tailored to provide a desired elution rate for one or more drugs and to provide sufficient quantities of bioactive agents without compromising the mechanics of the stent during deployment and use. It would be beneficial to have a drug-elution system that can be tailored to accommodate a variety of drugs for controlled time delivery. Furthermore, it would be beneficial to provide a drug-delivery stent with phased delivery of drugs in effective quantities.

SUMMARY OF THE INVENTION

One aspect of the invention provides a drug elution stent including a stent framework and a drug elution portion disposed on the stent framework. The drug elution portion includes a first sugar layer disposed on the stent framework, at least one therapeutic agent layer disposed on the first sugar layer and a second sugar layer disposed on the at least one therapeutic agent layer.

Another aspect of the invention provides a method of manufacturing a drug elution stent. The method includes the steps of providing a stent having a stent framework and coating at least a portion of the stent framework with a drug elution portion. The drug elution portion includes a first sugar layer disposed on the stent framework, at least one therapeutic agent layer disposed on the first sugar layer and a second sugar layer disposed on the at least one therapeutic agent layer The present invention is illustrated by the accompanying drawing of various embodiments and the detailed description given below. The drawings should not be taken to limit the invention to the specific embodiments, but are for explanation and understanding. The detailed description and drawings are merely illustrative of the invention rather than limiting, the scope of the invention being defined by the appended claims and equivalents thereof. The drawings are not drawn to scale. The foregoing aspects and other attendant advantages of the present invention will become more readily appreciated by the detailed description taken in conjunction with the accompanying drawings.

DETAILED DESCRIPTION

The invention will now be described by reference to the drawings wherein like numbers refer to like structures.

Figure 1:
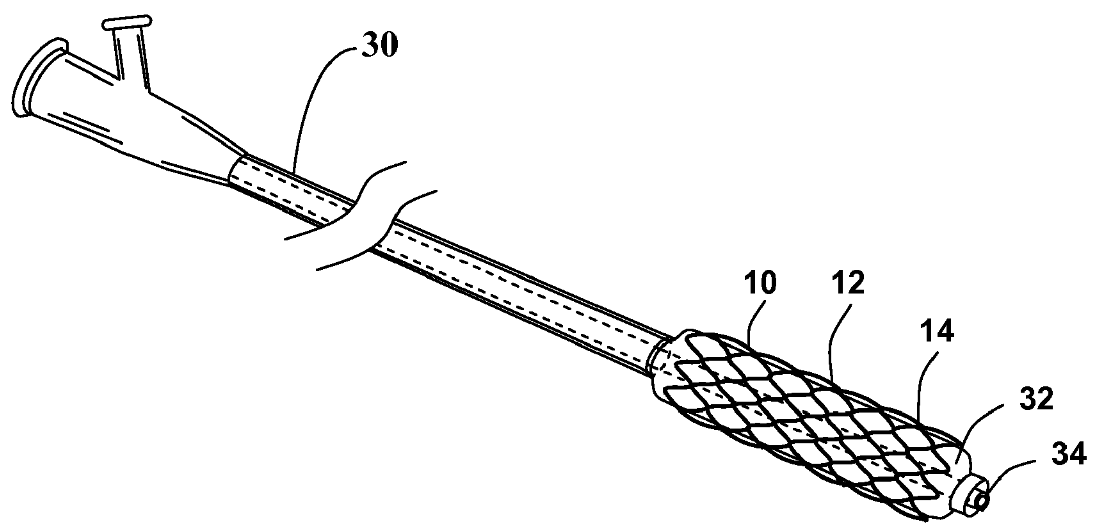
FIG. 1 is a schematic representation of a stent delivery system in accordance with the current invention.

FIG. 1 shows an illustration of a system 100 for treating a vascular condition, in accordance with one embodiment of the present invention. System 100 includes a drug elution stent 10 coupled to a delivery catheter 30. Drug elution stent 10 includes a generally tubular stent framework 12 and a drug elution portion 14.

The stent framework 12 may comprise a metallic base or a polymeric base. In one embodiment, the stent framework comprises a material selected from the group consisting of stainless steel, nitinol, tantalum, MP35N alloy, platinum, titanium, a suitable biocompatible alloy, a suitable biocompatible polymer, or a combination thereof.

Catheter 30, of an exemplary embodiment, includes a balloon 32 that expands and deploys the drug-elution stent within a vessel of the body. After positioning drug-elution stent 10 within the vessel with the assistance of a guide wire traversing through a guide wire lumen 34 inside catheter 30, balloon 32 is inflated by pressurizing a fluid such as a contrast fluid or saline solution that fills a tube inside catheter 30 and balloon 32. Drug-elution stent 10 is expanded until a desired diameter is reached, and then the contrast fluid is depressurized or pumped out, separating balloon 32 from stent 10 and leaving stent 10 deployed in the vessel of the body. Alternately, catheter 30 may include a sheath that retracts to allow expansion of a self-expanding stent 10. The stent is inserted typically in a controlled environment such as a catheter lab or hospital. A delivery catheter, which helps position the stent in a vessel of the body, is typically inserted through a small incision of the leg and into the femoral artery, and directed through the vascular system to a desired place in the vessel. Guide wires threaded through an inner lumen of the delivery catheter assist in positioning and orienting the stent framework. The position of the stent may be monitored, for example, with a fluoroscopic imaging system or an x-ray viewing system in conjunction with radiopaque markers on the stent, radiopaque markers on the delivery catheter, or contrast fluid injected into an inner lumen of the delivery catheter and into an inflatable catheter balloon that is coupled to the stent. The stent is deployed, for example, by expanding the stent framework with a balloon or by extracting a sheath that allows a self-expandable stent to enlarge after positioning the stent at a desired location within the body. Before clinical use, the stent is sterilized by using conventional medical means.

Drug elution portion 14 includes a biocompatible sugar and a therapeutic agent. For simplicity, as used herein, the term “sugar” includes sugar and sugar derivatives. Suitable biocompatible sugars and sugar derivatives include, but are not limited to, dextran, dextrose, glucose, sucrose, sorbose, galactose, glucosamine, mannitol, xylitol and combinations thereof. Those with skill in the art will recognize that other sugars and sugar derivatives not listed here are suitable for the present invention and are embraced within the scope of the disclosure.

Drug elution portion 14 is configured to resemble a "sandwich" wherein a layer of therapeutic agent is "sandwiched" between two layers of sugar. This is described in more detail below with relation to FIGS. 2 and 3.

Each layer or component of drug elution portion 14 may be disposed on the stent surface by any means known in the art such as, for example, by dip coating, by spray coating, by vacuum deposition or a combination thereof. In another embodiment, the drug elution portion 14 may be a preformed drug elution portion that is fixed to the stent framework. In one embodiment the preformed drug elution portion 14 is applied to the surface of the stent framework by a self adhesive comprising dextran. In one embodiment, the drug elution portion may be preformed by casting.

Figure 2:
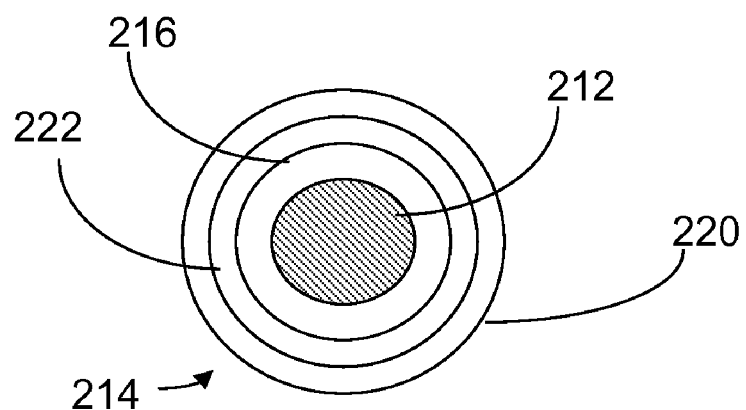
FIG. 2 is a cross-sectional view of one embodiment of a drug delivery stent, in accordance with the current invention.
Figure 3:
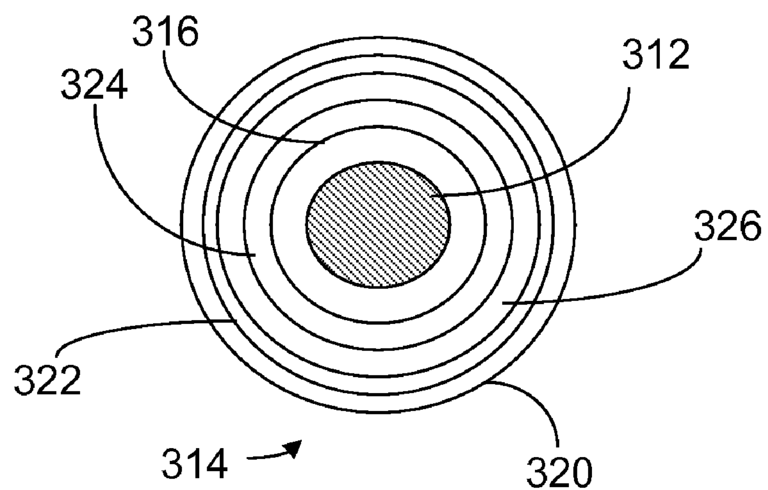
FIG. 3 is a cross-sectional view of another embodiment of a drug delivery stent, in accordance with the current invention.

FIGS. 2 and 3 illustrate cross-sections of two exemplary embodiments of a stent framework having a drug elution portion.

FIG. 2 illustrates a cross section of drug elution stent 200, in accordance with the present invention. Drug elution stent 200 comprises a stent framework 212 and a drug elution portion 214. In one embodiment, drug elution portion 214 includes a first interior sugar layer 216 disposed on stent framework 212, a second exterior sugar layer 220 and at least one therapeutic agent 222 carried between the first and second sugar layers 216, 220. In one embodiment, the sugar of sugar layers 216 and 220 is dextran. In another embodiment, the sugar is sucrose. Each layer, 216, 222 and 220 may be deposited on stent framework 212 and/or the underlying layer by those methods described above for FIG. 1.

In one embodiment, the second exterior sugar layer 220 is constructed and arranged to control an elution rate of at least one therapeutic agent. For example, in one embodiment, sugar layer 220 is hardened to a predetermined hardness to control the elution of the underlying therapeutic agent. The predetermined hardness may range from a relatively soft sugar layer that dissolves quickly once exposed to bodily fluids to a relatively hard or glassy layer that dissolves over an extended period of time such as from one day to several weeks. In one embodiment, the stent is coated with varying degrees of hardness of the exterior layer or portions of the exterior layer in order to elute the underlying therapeutic layer over a period of time ranging from one minute to several weeks. Sugar layer 220 may be hardened by drying, heating, chemical application or any other method known to those with skill in the art.

In another embodiment the elution rate is controlled by the thickness of the exterior sugar layer. In one embodiment, the thickness of the sugar layer 220 is between about 0.01-0.30 microns. In one embodiment, the thickness of layer 220 is between about 25.0-35 microns. In one embodiment, the total thickness of the drug elution portion is between about 0.01-30 microns. In another embodiment, the thickness of the sugar layer 220 is between about 5-20 microns.

FIG. 3 illustrates a cross section of drug elution stent 300, in accordance with the present invention. In this embodiment, drug elution portion 314 includes three sugar layers, 316, 320 and 326 and two therapeutic agent layers 322, 324. In this embodiment, drug elution portion 314 includes a first therapeutic agent 322, disposed between third intermediate sugar layer 326 and exterior sugar layer 320 and a second therapeutic agent 324, disposed between interior sugar layer 316 and third intermediate sugar layer 326.

In one embodiment, drug elution portion 314 may comprise a first therapeutic agent 322 having a first pharmaceutical characteristic and a second therapeutic agent 324 having a second pharmaceutical characteristic. In one embodiment, the drug elution portion 314 is constructed and arranged to elute the first and second therapeutic agents 322, 324 in a phased manner after the stent 300 is deployed. A third intermediate sugar layer 326 may be provided between the first and second sugar layers 322, 324, separating the first and second therapeutic agents 322, 324, such that each therapeutic agent is enveloped by sugar. In one embodiment, the intermediate sugar layer 326 is constructed and arranged to control the elution rate of second therapeutic agent 324. The sugar layers 316, 320, 326 and therapeutic agent layers 322, 324 may be applied the same as or similar to sugar layers 216, 220 and therapeutic layer 222 described above.

In one embodiment, the second exterior sugar layer 320 is constructed and arranged to control an elution rate of at least one therapeutic agent. For example, in one embodiment, sugar layer 320 is hardened to a predetermined hardness to control the elution of the underlying therapeutic agent. The predetermined hardness may range from a relatively soft sugar layer that dissolves quickly once exposed to bodily fluids to a relatively hard or glassy layer that dissolves over an extended period of time such as from one day to several weeks. In one embodiment, the stent is coated with varying degrees of hardness of the exterior layer or portions of the exterior layer in order to elute the underlying therapeutic layer over a period of time ranging from one minute to several weeks. Sugar layer 320 may be hardened by drying, heating, chemical application or any other method known to those with skill in the art.

In another embodiment the elution rate of therapeutic agent layers 322, 324 is controlled by the thickness of the sugar layers 320, 326. In one embodiment, the thickness of sugar layers 320, 326 is between about 0.01-0.30 microns. In one embodiment, the thickness of sugar layers 320, 326 is between about 25.0-35 microns. In another embodiment, the thickness of sugar layer 320 is between about 25.0-35 microns and the thickness of sugar layer 326 is between about 0.01-0.30 microns. In another embodiment, the total thickness of the drug elution portion is between about 0.1-30 microns. In another embodiment, the thickness of the sugar layer 320 is between about 5-20 microns and the thickness of sugar layer 326 is between about 5-20 microns.

In one embodiment, therapeutic agent 322 and/or 324 is attached to a carrier. In another embodiment therapeutic agent 322 and/or 324 is provided in a dextran or dextran-containing layer. For example, a therapeutic compound or drug may be dissolved in the dextran or dextran-containing material prior to application to the stent.

The term "therapeutic agent" includes one or more "therapeutic agents" or "drugs". The terms "therapeutic agent(s)" and "drug(s)" are used interchangeably. The drug elution portion may include any suitable therapeutic agent or drug known in the art. In one embodiment, the therapeutic agent is selected from the group consisting of an antisense agent, an antineoplastic agent, an antiproliferative agent, an antithrombogenic agent, an anticoagulant, an antiplatelet agent, an antibiotic, an anti-inflammatory agent, a therapeutic peptide, a gene therapy agent, a therapeutic substance, an organic drug, a pharmaceutical compound, a recombinant DNA product, a recombinant RNA product, a collagen, a collagenic derivative, a protein, a protein analog, a saccharide, a saccharide derivative, or a combination thereof.

A drug elution stent of the present invention and as described herein has many different possible applications. The stent may be used in the cardiovascular system (e.g., in the coronary artery, femoral artery, peripheral arteries or other arteries in the body), the cerebrovascular system, urogenital systems, biliary conduits, abdominal passageways, the gastrointestinal tract or other biological vessels in the body. For example, the stent may be an esophageal stent or biliary stent. Treatment of vascular conditions may include the prevention or correction of various ailments and deficiencies associated with the cardiovascular system, the cerebrovascular system, urogenital systems, biliary conduits, abdominal passageways and other biological vessels within the body. Insertion of the drug elution stent 10 in a vessel in the body may help treat, for example, heart disease, various cardiovascular ailments, and other vascular conditions. Catheter-deployed drug elution stent 10 typically is used to treat one or more blockages, occlusions, stenoses, or diseased regions in the coronary artery, femoral artery, peripheral arteries, and other arteries in the body. While the drug elution portion has been described herein in combination with a stent, it may be applied to other implantable medical devices suitable for drug delivery. For example, the drug elution portion may be used in guidewires, catheters (including balloon angioplasty catheters), or filters (including vena cava filters). The drug elution portion may also be applied to other implantable and blood-contacting biomedical devices such as coated pacemaker leads, microdelivery pumps, feeding and delivery catheters, heart valves, artificial livers and other artificial organs.

Figure 4:
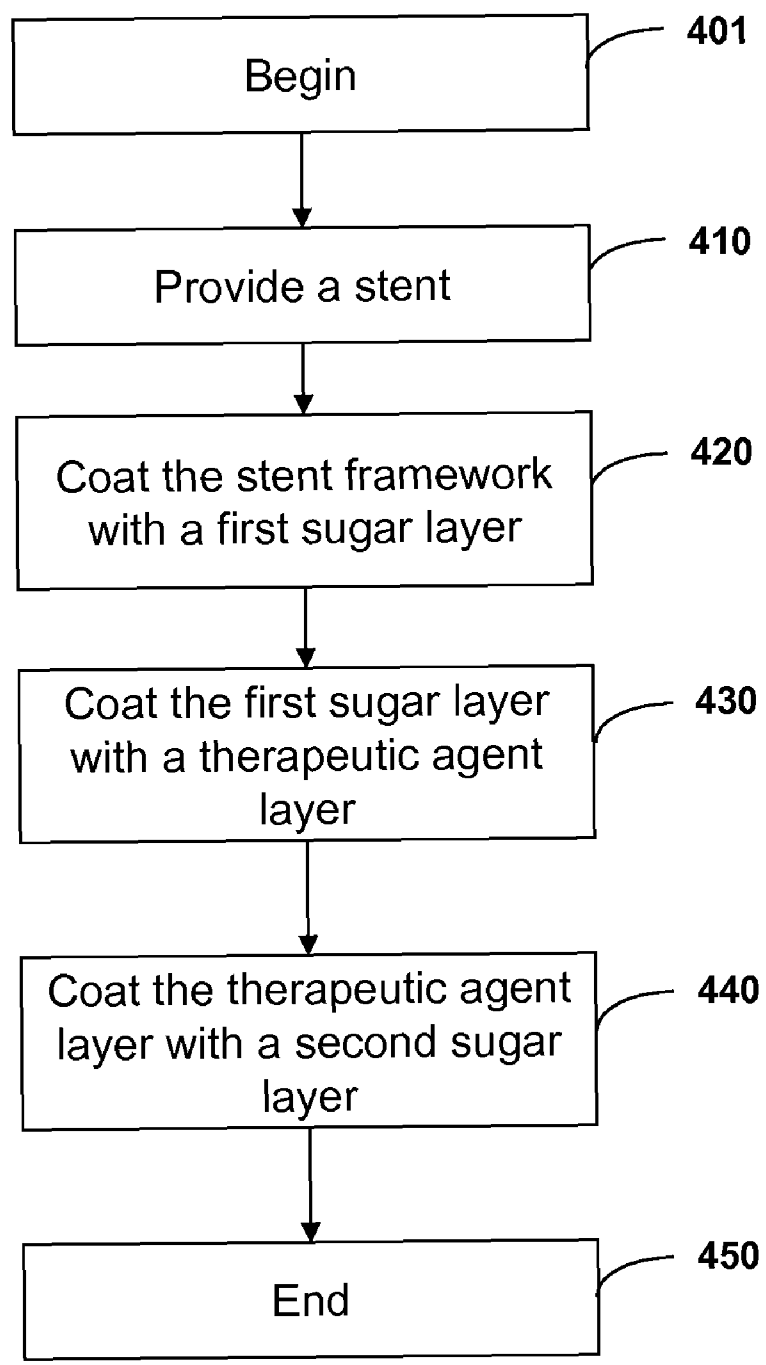
FIG. 4 is a flow diagram of a method for manufacturing a drug-polymer stent, in accordance with one embodiment of the current invention.

FIG. 4 is a flow diagram of a method 400 for manufacturing a drug elution stent, in accordance with one embodiment of the current invention. Method 400 begins at 401. In one embodiment, method 400 includes providing a stent 410. At steps 420 to 440, a drug elution portion is applied to the stent framework. At step 420, the stent framework of the provided stent is coated with a first sugar layer. At step 430, a first layer of therapeutic agent is disposed on the surface of the first sugar layer. Next, a second sugar layer is disposed on the first therapeutic agent layer, step 440. At this stage of method 400, the cross section of the coated stent framework is similar to that illustrated in FIG. 2. Those with skill in the art will appreciate that steps 420 to 440 can be repeated as required for a particular application and that the number of layers of sugar and therapeutic agent may be increased to suit a particular application. In one embodiment, Steps 430 and 440 are repeated to provide a stent having a cross section similar to or the same stent 300 illustrated in FIG. 3. Those with skill in the art will also recognize that before a next layer is disposed on a previously coated layer the previously coated layer may be allowed to dry or cure using any method known in the art.

In one embodiment, the outer most sugar layer is hardened to provide a predetermined controlled elution rate. In another embodiment, an intermediate sugar layer is hardened to control the elution rate of an underlying therapeutic agent. In another embodiment, at least one intermediate sugar layer and the outer sugar layer are hardened to control the elution rate of the therapeutic agent immediately underlying each respective sugar layer. The thickness of each layer may be the same as or similar to the thicknesses described above.

The drug elution portion may be provided by dip coating, spray coating or a combination thereof. In one embodiment, the drug elution portion may be a preformed drug elution portion that is affixed to the stent. In one embodiment, the drug elution portion may be applied by a self adhesive comprising dextran. The drug elution portion may be preformed by casting. Method 400 ends at step 450.

Figure 5:
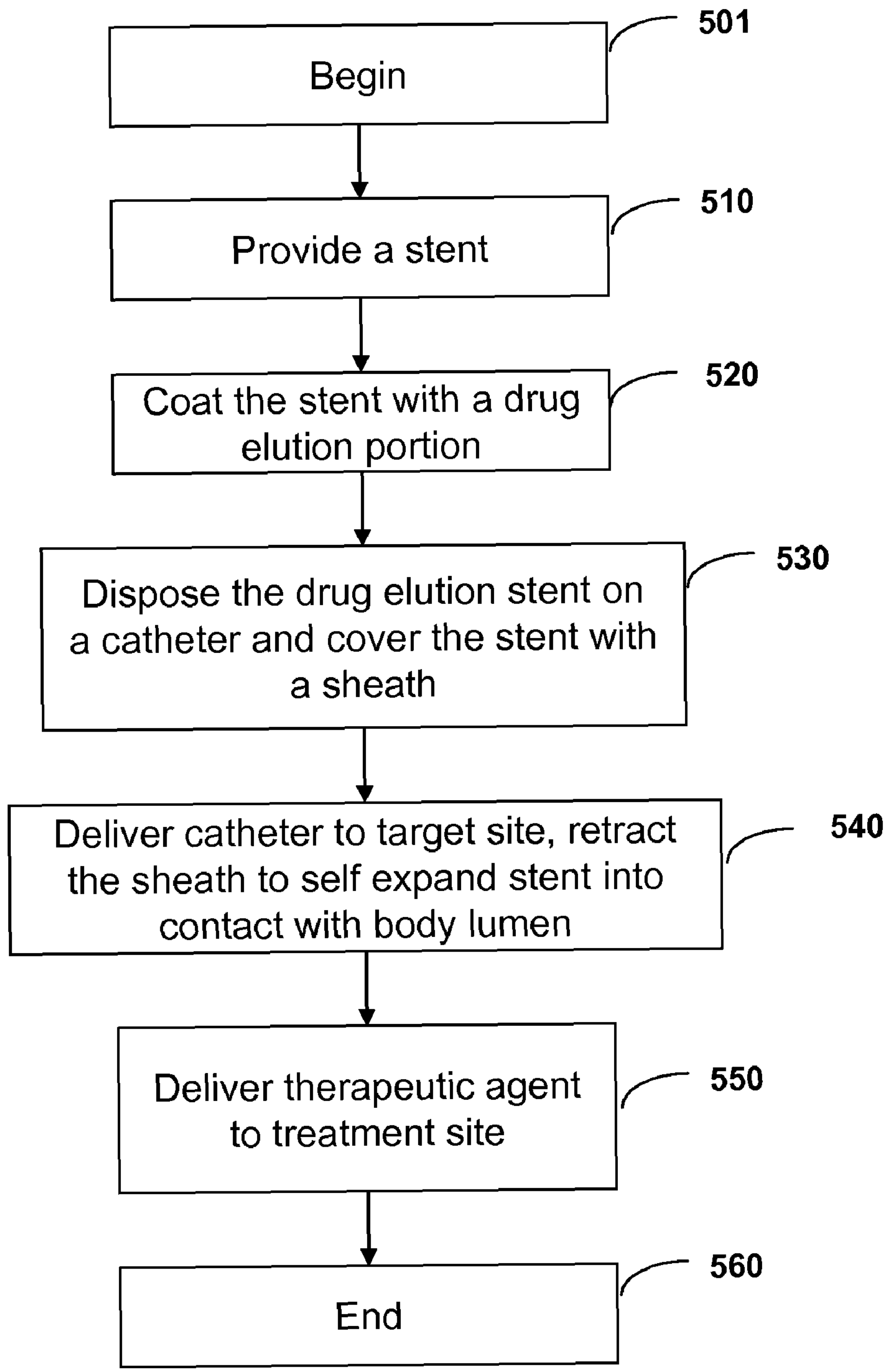
FIG. 5 is a flow diagram of a vascular treatment method in accordance with one embodiment of the current invention.

FIG. 5 is a flow diagram of a method 500 for delivery of a self expanding drug elution stent. Method 500 begins at step 501. A self expanding stent is provided (step 510) and coated with a drug elution portion, at step 520. The stent provided at step 510 may be coated with the drug elution portion using method 400 described above and illustrated in FIG. 4. The stent is disposed on a catheter and covered by a restraining sheath, at step 530. Next, at step 540, the coated stent is delivered to the target site and the sheath is retracted in order to expand the stent into contact with the body lumen. Once delivered, the therapeutic agent is delivered to the treatment site over a predetermined period of time, at step 550. Method 500 ends at step 560.

Figure 6:
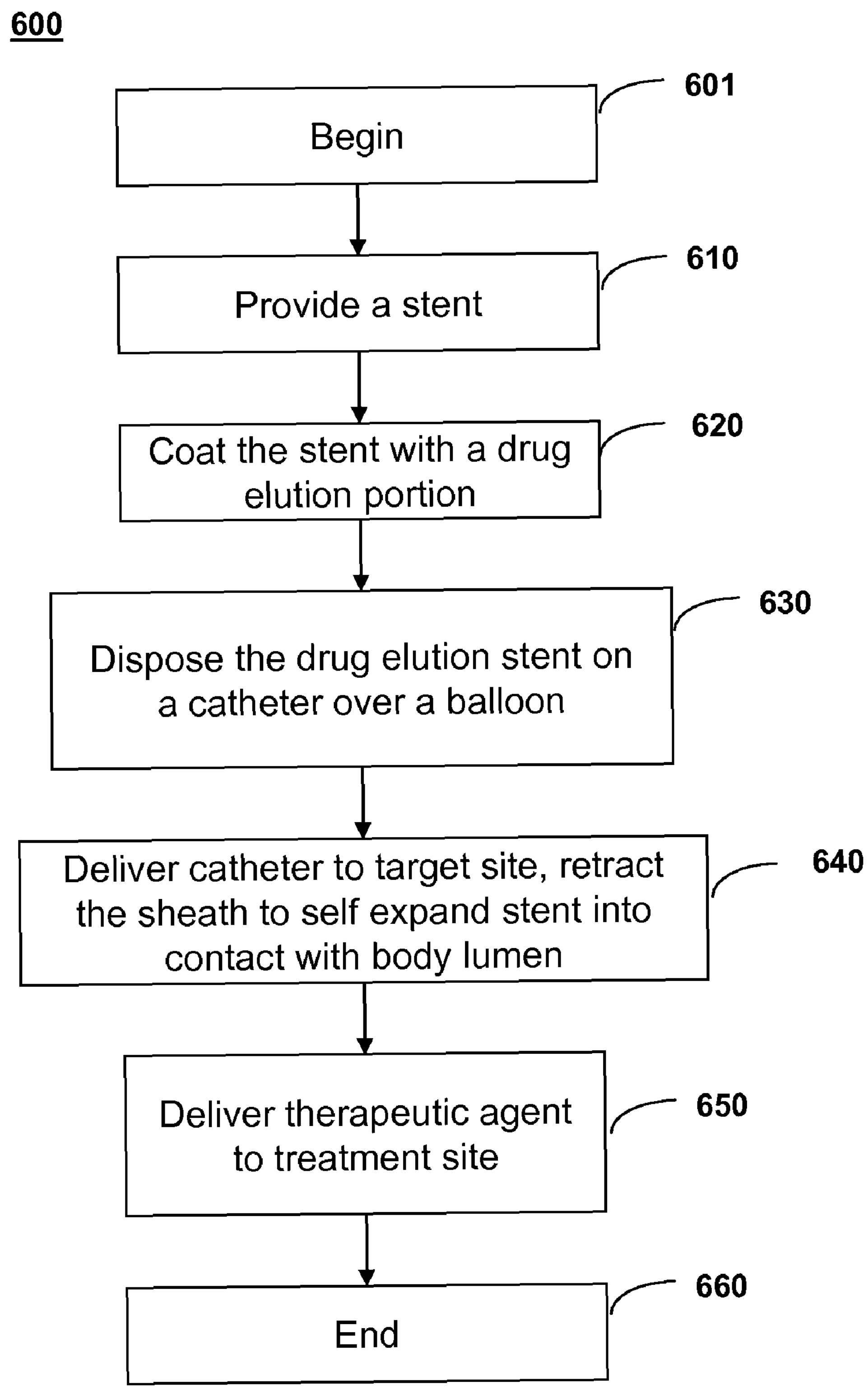
FIG. 6 is a flow diagram of a vascular treatment method in accordance with another embodiment of the current invention.

FIG. 6 is a flow diagram of a method 600 for delivery of a balloon-expandable stent. Method 600 begins at step 601. A balloon expandable stent is provided (step 610) and coated with a drug elution portion, at step 620. The stent provided at step 610 may be coated with the drug elution portion using method 400 described above and illustrated in FIG. 4. The stent is disposed on a catheter over a balloon, at step 630. Next, at step 640, the coated stent is delivered to the target site and the balloon is expanded to expand the stent into contact with the lumen. Once delivered, the therapeutic agent is delivered to the treatment site over a predetermined period of time, at step 650. Method 600 ends at step 660.

While the invention has been described with reference to particular embodiments, it will be understood by one skilled in the art that variations and modifications may be made in form and detail without departing from the spirit and scope of the invention.

What is claimed is:

1. A drug elution stent comprising:
a stent framework; and
a drug elution portion disposed on the stent framework, wherein the drug elution portion comprises:
a first sugar layer disposed on the stent framework;
at least one therapeutic agent layer disposed on the first sugar layer, the at least one therapeutic agent layer consisting of one or more therapeutic agents; and
a second sugar layer disposed on the at least one therapeutic agent layer, the second sugar layer being a hard, glassy layer.

2. The drug elution stent of claim 1 wherein the at least one of the first sugar layer and the second sugar layer comprises dextran.

3. The drug elution stent of claim 2 wherein the second sugar layer is configured to control an elution rate of the at least one therapeutic agent.

4. The drug elution stent of claim 3 wherein the second sugar layer is hardened to a predetermined hardness to control the elution rate of the at least one therapeutic agent.

5. The drug elution stent of claim 3 wherein the second sugar layer has a thickness of between 25 and 35 microns.

6. The drug elution stent of claim 3 wherein the second sugar layer has a thickness of between 5 and 20 microns.

7. The drug elution stent of claim 3 wherein the at least one therapeutic agent comprises a first therapeutic agent having a first pharmaceutical characteristic and a second therapeutic agent having a second pharmaceutical characteristic, the second sugar layer of dextran on the exterior being constructed and arranged to elute the first and second therapeutic agents in a phased manner after the stent is deployed.

8. The drug elution stent of claim 1 further comprising:
a second therapeutic agent layer disposed on the second sugar layer and a third sugar layer disposed on the second therapeutic agent layer.

9. The drug elution stent of claim 8 wherein the third sugar layer is configured to control an elution rate of the at least one therapeutic agent.

10. The drug elution stent of claim 9 wherein the third sugar layer is hardened to a predetermined hardness to control the elution rate of the second therapeutic agent layer.

11. The drug elution stent of claim 9 wherein the third sugar layer has a thickness of between 25 and 35 microns.

12. The drug elution stent of claim 9 wherein the third sugar layer has a thickness of between 5 and 20 microns.

13. The stent of claim 1 wherein the stent framework comprises one of a metallic base or a polymeric base.

14. The stent of claim 1 wherein the stent framework base comprises a material selected from the group consisting of stainless steel, nitinol, tantalum, MP35N alloy, platinum, titanium, a suitable biocompatible alloy, a suitable biocompatible polymer, or a combination thereof.

15. The stent of claim 1 wherein the therapeutic agent is selected from the group consisting of an antisense agent, an antineoplastic agent, an antiproliferative agent, an antithrombogenic agent, an anticoagulant, an antiplatelet agent, an antibiotic, an antiinflammatory agent, a therapeutic peptide, a gene therapy agent, a therapeutic substance, an organic drug, a pharmaceutical compound, a recombinant DNA product, a recombinant RNA product, a collagen, a collagenic derivative, a protein, a protein analog, a saccharide, a saccharide derivative, or a combination thereof.

16. A method of manufacturing a drug elution stent, the method comprising:

providing a stent having a stent framework; and coating at least a portion of the stent framework with a drug elution portion, wherein the drug elution portion comprises:

a first sugar layer disposed on the stent framework;

at least one therapeutic agent layer disposed on and immediately adjacent to the first sugar layer, the at least one therapeutic agent layer consisting of one or more therapeutic agents; and a second sugar layer disposed on and immediately adjacent to the at least one therapeutic agent layer, the second sugar layer being a hard, glassy layer.

17. The method of claim 16 further comprising:

controlling the elution rate of the at least one therapeutic agent.

18. The method of claim 17 wherein controlling the elution rate comprises providing a second sugar layer having a thickness between 25 and 35 microns.

19. The method of claim 17 wherein controlling the elution rate comprises hardening the second sugar layer to a predetermined hardness.

20. The method of claim 16 wherein coating the stent framework comprises dip coating or spray coating.

21. The method of claim 16 further comprising disposing a second therapeutic agent layer on the second sugar layer and disposing a third sugar layer on the second therapeutic layer.

22. A stent delivery system comprising:

a catheter;

a stent disposed on a distal end of the catheter, the stent having a stent framework; and a drug elution portion disposed on the stent framework, wherein the drug elution portion comprises:

a first sugar layer disposed on the stent framework;

at least one therapeutic agent layer disposed on the first sugar layer, the at least one therapeutic agent layer consisting of one or more therapeutic agents; and a second sugar layer disposed on the at least one therapeutic agent layer, the second sugar layer being a hard, glassy layer.

23. The drug elution stent of claim 1 wherein the second sugar layer is outermost of all layers disposed on the stent framework.

24. The drug elution stent of claim 8 wherein the third sugar layer is outermost of all layers disposed on the stent framework.

* * * * *